(12) United States Patent
Sabatier et al.

(10) Patent No.: US 9,795,551 B2
(45) Date of Patent: Oct. 24, 2017

(54) TETRAPEPTIDES AND A METHOD OF USE AS AN ANTIOXIDANT

(71) Applicant: L'OREAL, Paris (FR)

(72) Inventors: Jean-Marc Sabatier, Rousset (FR); Zhi Pan, Ridgewood, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/315,585

(22) Filed: Jun. 26, 2014

(65) Prior Publication Data
US 2015/0374606 A1    Dec. 31, 2015

(51) Int. Cl.
| | | |
|---|---|---|
| *A61K 38/00* | (2006.01) | |
| *A61K 8/64* | (2006.01) | |
| *C07K 5/117* | (2006.01) | |
| *A61Q 19/00* | (2006.01) | |
| *A61Q 5/00* | (2006.01) | |
| *A23L 3/3544* | (2006.01) | |
| *C07K 5/09* | (2006.01) | |
| *A23L 3/3526* | (2006.01) | |

(52) U.S. Cl.
CPC .............. *A61K 8/64* (2013.01); *A23L 3/3526* (2013.01); *A23L 3/3544* (2013.01); *A61Q 5/00* (2013.01); *A61Q 19/00* (2013.01); *C07K 5/0817* (2013.01); *C07K 5/1024* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2002/0103228 | A1* | 8/2002 | Sankaranarayanan | ........ 514/336 |
| 2004/0002441 | A1* | 1/2004 | Segall et al. | ....................... 514/2 |

FOREIGN PATENT DOCUMENTS

| | | |
|---|---|---|
| CN | 1593646 A | 3/2005 |
| JP | 2006342107 A | 12/2006 |
| WO | WO2004091569 A2 | 10/2004 |

OTHER PUBLICATIONS

Rushworth et. al. British Journal of Pharmacology (2009), 157, 1186-1188.*
Kim et al. Biotechnol. Bioprocess Eng. 2001, 6: 244-251.*
U.S. Appl. No. 14/315,619, filed Jun. 26, 2014, Young.
Gulizar Atmaca, "Antioxidant Effects of Sulfur-Containing Amino Acids" Yonsei Medical Journal, vol. 45, No. 5, (pp. 776-788), 2004.
Hailong Yang, et al., "Antioxidant Peptidomics Reveals Novel Skin Antioxidant System" Research, Skin Antioxidant Peptidomics, Molecular & Cellular Proteomics 8.3, This pa;er is available on line at http://www.mcponline.org, 2009 by The American Society for Biochemistry and Molecular Biology, Inc. (pp. 571-583) 2009.
Mingsheng Xu, et al., "Antioxidative Activity of Hen Egg Ovalbumin Hydrolysates" Original Article, Asia Pac J Clin Nutr 2007; 16 (suppl 1): (pp. 178-182).
Hau-Ming Chen, et al., "Antioxidative Properties of Histidine-Containing Peptides Designed from Peptide Fragments Found in the Digests of a Soybean Protein" Published on Web Jan. 19, 1998, American Chemical Society, J. Agric. Food Chem., vol. 46, No. 1, 1998 (pp. 49-53).
Alexander A. Boldyrev, et al., "Carnosine, the Protective, Anti-aging Peptide" Bioscience Reports, vol. 19, No. 6, 1999, (pp. 581-587).
Kesheng Zhao, et al., "Cell-Permeable Peptide Antioxidants Targeted to Inner Mitochondrial Membrane Inhibit Mitochondrial Swelling, Oxidative Cell Death, and Reperfusion Injury" JBC, The Journal of Biological Chemistry, Affinity Sites, J. Biol. Chem. 2004, vol. 279, No. 33, (pp. 34682-34690).
Shaheen B. Mowla, et al., "A novel Stress-inducible Antioxidant Enzyme Identified from the Resurrection Plant Xerophyta Viscosa Baker" Original Article, Planta (2002) 215: (pp. 716-726).
Barbara S. Berlett, et al., "Protein Oxidation in Aging, Disease, and Oxidative Strees" Minireview, JBC, The Journal of Biological Chemistry, Affinity Sites, J. Biol. Chem. 1997, vol. 272, No. 33, (pp. 20313-20316).

* cited by examiner

*Primary Examiner* — Jeanette Lieb
(74) *Attorney, Agent, or Firm* — Oblon, McClelland, Maier & Neustadt, L.L.P.

(57) ABSTRACT

A tetrapeptide having antioxidant activity is provided. The tetrapeptide has a structure comprising, in amino acid sequence from N-terminus to C-terminus: tryptophan-X-tyrosine-X; wherein X is arginine, lysine, histidine or any positively-charged amino acid derivative such as 5-hydroxylysine, ornithine, 2,4-diamino-butyrate and 2,3-diamino-propionate. Each amino acid of the sequence or its Homo-amino acid derivative is independently of the D configuration (D-stereoisomer) or of the L configuration (L-stereoisomer), and the C-terminal comprises one selected from the group consisting of carboxyl (—COOH), and carboxamide (—CONH$_2$). A composition stabilized to oxidation or having antioxidant activity and a method for attenuating effects of free radicals on a keratinous material are also provided.

19 Claims, No Drawings

TETRAPEPTIDES AND A METHOD OF USE AS AN ANTIOXIDANT

BACKGROUND OF THE INVENTION

Antioxidants are compounds which can delay or inhibit the oxidation of organic molecules by inhibition of the initiation and/or propagation of oxidizing chain reactions, generally free radical reactions. Species associated with free radical oxidation processes include peroxyl radicals (ROO.), superoxide radicals ($O_2.^-$) and hydroxyl radicals (.OH). Many natural and synthetic molecules have antioxidant properties and such character has been quantified, collected and published by the United States Department of Agriculture by listing of oxygen radical absorbance capacities (ORAC). Generally, a wide range of spices, fruits, berries and legumes have been identified as having antioxidant properties. Natural antioxidants provide platforms for the quenching of free radicals.

Conventionally employed biologically safe antioxidants include Vitamin C, Carnosine, Glutathione and Resveratrol. Carnosine (β-alanyl-histidine) is a natural dipeptide that is innate to vertebrates and found to act as a pH buffer, ion-chelating agent and in lipid peroxidation in vitro. Such activity for Carnosine spurs interest in peptide structures, because peptides offer a wide variety of structural modification and molecular design possibilities upon which antioxidant molecules of designed properties may be prepared.

Proteins have also been shown to have antioxidative activities against free radical oxidation of lipids and/or fatty acids. Certain peptides having electron donor properties can react with free radicals to terminate the radical chain reaction, although the exact mechanism of action for such antioxidant peptides is not clearly known. Enzymes involved in anti-oxidation reactions (e.g. superoxide dismutase (SOD), catalase, glutathione peroxidase) play an important role in cellular defense against oxidative stresses. However, there are many issues existing for direct application of such natural redox proteins as antioxidants including bioavailability, safety, stability and cost. Some aromatic amino acids and histidine have been reported to play a vital role in peptides having antioxidant properties.

In view of growing demand for antioxidants designed for attractive cost and structure activity performance that may be used in food, cosmetic and other applications, economical antioxidants based on natural product raw material building blocks are sought. Proteins or long chain polypeptides having interesting antioxidant properties are known; however, the cost of producing synthetic peptides are five to twenty times higher than the cost of conventional antioxidants.

Therefore, the present inventors have analyzed the amino acid sequences of selected redox proteins and have identified short active motifs (less than 6 amino acid residues in length) that possess antioxidant activity. A study of antioxidant properties of short polypeptide molecules has identified specific structure activity relationships which have led to the surprising discovery of cost effective short chain polypeptides having antioxidant activity comparable to or better than conventionally known antioxidants such as Vitamin C and Carnosine.

Therefore an object of the present invention is to discover novel short chain polypeptides containing six amino acid residues or less that have high antioxidant activity and are structurally tailored for specific utility. The short chain polypeptides must be biologically safe and ideally at least economically competitive with the conventionally employed antioxidants. In addition, the amino acid content of the short chain polypeptides will not include the sulfur containing amino acids cysteine and methionine, thus avoiding possible odor problems in production and utilization.

A further object of the present invention is to provide a method to protect a composition from oxidation or to impart antioxidant properties to a composition.

An even further objective of the present invention is to provide a method to protect a keratinous material from free radical degradation.

SUMMARY OF THE INVENTION

These and other objects have been achieved by the present invention, the first embodiment of which includes a tetrapeptide having a structure comprising, in amino acid sequence from N-terminus to C-terminus:

tryptophan-X-tyrosine-X;

wherein X is arginine, lysine, histidine or any positively-charged amino acid derivative such as 5-hydroxylysine, ornithine, 2,4-diamino-butyrate and 2,3-diamino-propionate. Each amino acid of the sequence or its Homo-amino acid derivative is independently of the D configuration (D-stereoisomer) or of the L configuration (L-stereoisomer), and the C-terminal comprises one selected from the group consisting of carboxyl (—COOH), carboxamide (—$CONH_2$) and —$CH_2OH$.

In another embodiment, the present invention includes a method for attenuating effects of free radicals and reactive oxygen species on a keratinous material wherein the tetrapeptide of the first embodiment is applied to the keratinous material in the form of a composition in a physiologically acceptable medium.

The foregoing paragraphs have been provided by way of general introduction, and are not intended to limit the scope of the following claims. The described embodiments, together with further advantages, will be best understood by reference to the following detailed description taken in conjunction with the appended claims.

DETAILED DESCRIPTION OF THE PREFERRED EMBODIMENTS

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where a numerical limit or range is stated, the endpoints are included. Also, all values and subranges within a numerical limit or range are specifically included as if explicitly written out.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

In the following description peptide sequences are described in terms of one-letter abbreviations of the amino acids according to the following chart.

| Amino acid | Abbreviation | Amino Acid | Abbreviation | Amino Acid | Abbreviation |
|---|---|---|---|---|---|
| Alanine | A | Arginine | R | Asparagine | N |
| Aspartate | D | Cysteine | C | Glutamate | E |
| Glutamine | Q | Glycine | G | Histidine | H |
| Isoleucine | I | Leucine | L | Lysine | K |
| Methionine | M | Phenylalanine | F | Proline | P |
| Serine | S | Threonine | T | Tryptophan | W |
| Tyrosine | Y | Valine | V | | |

The capital case letters represent naturally occurring amino acids in the L configuration. When a lower case letter is shown, the amino acid is in the D configuration.

According to conventional practice amino acid sequence description is provided by the one letter abbreviation sequence stated with the N-terminal end (N-terminus) amino acid first in the amino acid sequence and ending with the carboxyl terminal (carboxy terminus) amino acid. For example, the sequence RYHM is a polypeptide containing four amino acid residues linked via peptide bonds (—CONH—) in the order from N-terminus to carboxy terminus: arginine-tyrosine-histidine-methionine. When the carboxyl terminus of the sequence is designated with —$NH_2$, the end carboxyl group is in the form of an amide (—$CONH_2$).

When the N terminal group is derivatized, the nature of the derivative is designated by standard organic chemistry abbreviations. For example, "Ac" indicates an acetyl group ($CH_3CO$—).

Throughout the following description, terms such as "polypeptide," "short chain polypeptide" and peptide molecule may be used interchangeably. According to the present invention, a short chain polypeptide contains 2 to 10 amino acid residues linked through a series of peptide bonds.

As understood by one of ordinary skill, the amino acids may be grouped according to the chemical structure of the side chain. Thus glycine, alanine, valine, leucine, isoleucine, methionine, tryptophan, phenylalanine and proline are described as nonpolar (hydrophobic) amino acids. Serine, threonine, cysteine, tyrosine, asparagine and glutamine are described as polar (hydrophilic), neutrally charged amino acids. Aspartic acid (aspartate) and glutamic acid (glutamate) are ionic (acidic) with a negative charge and lysine, arginine and histidine are ionic (basic) with a positive charge.

Standard abbreviations conventionally employed in organic chemistry may also be employed.

In the study of and search for molecules that have potent antioxidant activity and at the same time are biologically safe, economical to produce and may be tailored for physical properties including bioavailability, solubility and dispersibility, the inventors have recognized that polypeptides are an interesting class of molecules that have the potential to meet all the criteria for development of novel new antioxidants.

Thus, a study was undertaken to understand the structural property and molecular composition parameters of polypeptide molecules that contribute to maximum antioxidant activity. From this study a key WRYR sequence derived from region 157-160 of human extracellular SOD3 (Cu—Zn tetramer) was identified. Variations and derivatives as exemplified Table 1 of the Example were prepared and evaluated for antioxidant activity. These tetrapeptides demonstrate significant and unexpected antioxidant activity that is higher or broader than the conventional antioxidants Vitamin C and Carnosine.

Thus, the first embodiment of the present invention is a tetrapeptide having a structure comprising, in amino acid sequence from N-terminus to C-terminus:

tryptophan-X-tyrosine-X;

wherein X is arginine, lysine, histidine or any positively-charged amino acid derivative such as 5-hydroxylysine, ornithine, 2,4-diamino-butyrate and 2,3-diamino-propionate. Each amino acid of the sequence or its Homo-amino acid derivative is independently of the D configuration (D-stereoisomer) or of the L configuration (L-stereoisomer), and the C-terminal comprises one selected from the group consisting of carboxyl (—COOH) and carboxamide (—$CONH_2$).

Table I shows a compilation of polypeptides studied by the inventors to ascertain those elements of the molecular structure that contribute to or negate antioxidant activity. In the course of the study, polypeptides were prepared by conventional solid-phase chemical peptide synthesis methods (Fmoc/tButyl strategy) and screened in tubo for antioxidant activity.

In the screening standard testing for oxygen radical absorbance capacity (ORAC) and hydroxyl radical absorbance capacity (HORAC) were conducted with the test polypeptides. Testing was conducted according to USTM 190 (HORAC) and USTM 192 (ORAC). Upon review of the results as indicated in Table I, the inventors have discovered certain elements of the polypeptide structure as recited in claim 1 that are key contributors to determination of antioxidant activity.

The structural formulas, single letter abbreviation, ORAC and HORAC test results of the novel polypeptides are shown in Table I. Also shown in Table I are antioxidant results for Vitamin C and Carnosine. As indicated in Table I, the polypeptides according to the present invention have ORAC and HORAC activity comparable or better than the conventional antioxidants. Such activity is an unexpected and significant improvement obtained with the compounds of the present invention.

As indicated by the results of Table I, the individual amino acids of the polypeptide may be of the D- or L-configuration and significant antioxidant activity is retained. Thus, in a specific embodiment shown in Table 1 the tetrapeptide may have the structure:

WRYR—$NH_2$.

In another specific embodiment, the tetrapeptide may have the structure:

WRYR

In a further specific embodiment, the tetrapeptide may have the structure:

However, as indicated, by structural variation within the elements of the present invention and by methods known to one of ordinary skill in the art, the tetrapeptide structure may be tailored to obtain target antioxidant and physical properties including solubility and bioavailability. Elements according to which the structure may be tailored include variation between arginine, lysine, histidine and any positively-charged amino acid derivative such as 5-hydroxylysine, ornithine, 2,4-diamino-butyrate, 2,3-diamino-propionate and their Homo-amino acid derivatives, variation of the D- or L-stereoisomer of the individual amino acids and their derivatives and chemical modification of the N- and C-terminal extremities.

In one embodiment, the peptide bond (—CONH—) may be replaced by peptide bond isosters/surrogates, such as carba (—$CH_2CH_2$—), retro-inverso (—NHCO—), reduced/methyleneamino (—$CH_2NH$—), ketomethylene (—$COCH_2$—), retro-reduced (—$NHCH_2$—), thioamide (—CSNH—), methyleneoxy (—$CH_2O$—), depsi (—COO—) and alkene (—CH═CH—).

In a further embodiment, the present invention includes a composition comprising the polypeptide, according to the first embodiment of the invention. A short chain polypeptide of the invention may be advantageously formulated in a composition that may be in any galenical form normally available for the intended indication and mode of administration. The composition may comprise a physiologically or pharmaceutically acceptable medium.

According to one embodiment, a topical composition according to the invention may advantageously be formulated in any galenical form that is suitable for caring for the skin and its integuments, and may be in the form of ointments, creams, solutions, gels, emulsions, foams or aerosol compositions containing a propellant, milks, pomades, powders, impregnated pads, lotions or suspensions. A composition intended for topical administration may be an aqueous, aqueous-alcoholic or oily solution, a solution or a dispersion of the lotion or serum type, an emulsion of liquid or semiliquid consistency of the milk type, obtained by dispersing a fatty phase in an aqueous phase (O/W) or conversely (W/O), a suspension or an emulsion, of soft, semisolid or solid consistency, of the cream type or of the aqueous or anhydrous gel type, a multiple emulsion (W/O/W or O/W/O), a microemulsion, a nanoemulsion, a preparation of microcapsules, a preparation of microparticles, a vesicular dispersion of ionic and/or nonionic type, or a wax/aqueous phase dispersion.

In the case of a composition in accordance with the invention for oral administration, the use of an ingestible support, whose nature is adapted according to the type of composition under consideration, is preferred. Tablets, gel capsules or lozenges, suspensions, oral supplements in dry form and oral supplements in liquid form, milk, yoghurt, cheese, fermented milks, milk-based fermented products, ice creams, cereal-based products or fermented cereal-based products, milk-based powders, infant and baby formulae, food products of confectionery, chocolate or cereal type, and animal feed in particular for pets, are thus especially suitable as food supports.

The term "oral composition" means, for example, nutritional, nutraceutical, cosmeceutical or pharmaceutical compositions comprising at least one compound according to the invention. The formulation of the oral compositions according to the invention may be performed via any common process known to those skilled in the art for producing drinkable solutions, coated tablets, gel capsules, gels, emulsions, tablets to be swallowed or chewed, capsules, especially soft or hard capsules, granules to be dissolved, syrups, solid or liquid foods and hydrogels allowing controlled release, food bars, powders, in compacted or non-compacted form, liquid solutions or suspensions, confectioneries, fermented milk, fermented cheeses, chewing gums, toothpastes or spray solutions.

A short chain polypeptide of the invention may moreover be formulated with the usual excipients and components for such oral compositions or food supplements, i.e. especially fatty and/or aqueous components, humectants, thickeners, preserving agents, texture agents, taste agents and/or coating agents, and/or antioxidants. The formulating agents and excipients for oral compositions, and especially for food supplements, are known in this field and will not be the subject of a detailed description herein.

A composition according to the invention may also comprise any formulating agent or any cosmetically or dermatologically acceptable additional active agent. The amounts of these various active agents are those conventionally used in the field under consideration, and are especially determined so as not to affect the desired properties for a compound of the invention or for a composition of the invention.

In another embodiment, the short chain polypeptides according to the present invention may be included in nutritional compositions as an antioxidant or stabilizer of the composition that may also function as a solubilizer or as a dispersant. In other aspects of this embodiment, the short chain polypeptides according to the invention may be combined with other antioxidants to stabilize a composition to a broad spectrum of oxidative degradation mechanisms. The composition may contain nutrient fats, oils and/or proteins and may be aqueous or oil based solutions or emulsions or dry powders. In addition to the conventional antioxidants described above, other antioxidants known to one of skill in the art may be employed in combination with the short chain polypeptides of the present invention. Examples of adjuvant antioxidants may include, but are not limited to butylated hydroxy toluene, α- or β-carotene, citric acid or a derivative thereof, p-aminobenzoic acid, tocopherols and vitamins e, k and q10. One of ordinary skill may formulate an effective anti-oxidant combination for a nutritional composition employing conventional laboratory test methods.

In another embodiment, the present invention provides a method for attenuating effects of free radicals on a keratinous material by application of the composition described above to the keratinous material. The keratinous material may be human skin or hair and the composition may be in the form of, for example, a sunscreen, a skin cream, a shampoo or a hair conditioner.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

EXAMPLES

Method of Peptide Synthesis

The peptides were chemically synthesized by the solid phase method using an automated peptide synthesizer (Applied A433). Peptide chains were assembled stepwise on 0.75 meq of Fmoc-amide resin (production of carboxyl-amidated peptides) using 1 mmol of Fmoc L-amino acids (or Fmoc D-amino acids).

The following reagents were used: Fmoc-amino acids (1 mmol), activator (0.5 M HOBT/HBTU in dimethylformamide), base (2 M diisopropylethylamine in N-methyl-pyrrolidone) and deprotecting mixture (20% piperidine in N-methyl-pyrrolidone).

After peptide chain assembly, peptidyl-resins were treated 2 h at room temperature with a mixture of TFA/water/phenol/thioanisole/ethanedithiol (92.5/2/1/2.5/2). The peptide mixtures were then filtered, and the filtrates were precipitated by adding cold diethylether. The crude peptides were pelleted by centrifugation (3,000 g; 10 min), and the supernatants were discarded.

Peptides were purified by C18 reversed-phase (RP) High Performance/Pressure Liquid Chromatography (HPLC) using an Onyx Jupiter column (250×10 mm, 5μ). Elution of the peptides was performed with a linear gradient of 0 to 40% acetonitrile in 0.1% TFA (run duration of 150 min). The collected fractions were analyzed for their peptide content by analytical C18 RP-HPLC (Onyx monolithic column, 100×4.6 mm). The target peptides were characterized by matrix-assisted laser desorption ionization-time-of-flight (MALDI-TOF) mass spectrometry.

The purity of each peptide sample tested was >98%.

The peptides were tested in tubo for their antioxidant properties and tested against reference/known antioxidants. The evaluation of the antioxidant properties were conducted by determination of the ORAC (USTM 192) and HORAC (USTM 190) test methods. The results are listed in Table I for the peptides of the invention and for the conventionally known antioxidants vitamin C and Carnosine. Peptides according to the present invention are listed in Table I. Table I shows the amino acid sequence of the peptide in one-letter abbreviation (IUPAC convention) and in tubo antioxidant test results.

TABLE I

| Name | Sequence | ORAC/ peroxyl, μmol GAE/g | HORAC/ hydroxyl, μmol GAE/g |
|---|---|---|---|
| Vitamin C | — | 4456 | 0 |
| Carnosine | Beta-alanine, L-histidine | 354 | 2099 |
| RED6 | WRYR-NH2 | 4488 | 1548 |
| RED18 | WrYr-NH2 | 4758 | 2982 |
| RED19 | WRYr-NH2 | 4350 | 1457 |
| RED20 | WrYR-NH2 | 4448 | 1666 |
| RED21 | WRyR-NH2 | 4816 | 2472 |
| RED22 | wRyR-NH2 | 5383 | 1686 |
| RED23 | WRYR | 4091 | 2089 |
| RED24 | wRYR-NH2 | 4077 | 2225 |
| RED25 | WKYK-NH2 | 4168 | 2476 |
| RED26 | RwRyR-NH2 | 4461 | No capacity |
| RED27 | Ac-wRyR-NH2 | 5342 | 735 |
| RED28 | wRyRy-NH2 | 5216 | No capacity |
| RED29 | wRyRw-NH2 | 5512 | No capacity |
| RED31 | wRwR-NH2 | 4652 | 1189 |
| RED32 | RyR-NH2 | 3385 | 230 |

As indicated the tetrapeptides according to the present invention having the empirical sequence "tryptophan-arginine-tyrosine-arginine" or "tryptophan-lysine-tyrosine-lysine" showed antioxidant activity both in ORAC and HORAC that is comparable to or better than vitamin C and carnosine. Moreover antioxidant activity may be tailored according to modification of the D- or L-configuration of the individual amino acids or chemical modification of the N and C terminal groups.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. An antioxidant having a structure comprising, in amino acid sequence from N-terminus to C-terminus:

tryptophan-X-tyrosine-X;

wherein

X is lysine, histidine or a positively-charged amino acid derivative, the C-terminal comprises carboxamide (—CONH2), each amino acid or amino acid derivative of the amino acid sequence is independently of a D- or L-configuration, and optionally, a peptide bond unit of the amino acid sequence is an isoster or surrogate peptide bond.

2. The antioxidant of claim 1, wherein at least one X is a positively charged amino acid derivative and the positively charged amino acid derivative is selected from the group consisting of 5-hydroxylysine, ornithine, 2,4-diamino-butyrate, 2,3-diamino-propionate and Homo-amino acid derivatives thereof.

3. The antioxidant of claim 1, wherein at least one peptide bond unit is an isoster or surrogate bond and the isoster or surrogate bond is selected from the group consisting of carba bond (—CH2CH2-), retro-inverso (—NHCO—), reduced/methyleneamino (—CH2NH—), ketomethylene (—COCH2-), retro-reduced (—NHCH2-), thioamide (—CSNH—), methyleneoxy (—CH2O—), depsi (—COO—) and alkene (—CH=CH—).

4. The antioxidant of claim 1, having the structure:

WKYK—NH2.

5. A composition, comprising the antioxidant of claim 1, in a physiologically or pharmaceutically acceptable medium.

6. The composition of claim 5, wherein the antioxidant is of the structure:

WKYK—NH$_2$.

7. The composition of claim 5, wherein a content of the antioxidant is from 0.01 to 40 wt % based on a total weight of the composition.

8. The composition of claim 5, further comprising another antioxidant that is not a short chain polypeptide.

9. The composition of claim 5, further comprising a nutritional ingredient selected from the group consisting of a fat, an oil and a protein.

10. The antioxidant of claim 1, wherein X is histidine.

11. The antioxidant of claim 1, wherein X is lysine.

12. The composition of claim 5, wherein the composition is a topical composition.

13. The composition of claim 5, wherein the composition is an oral composition.

14. A method for attenuating effects of free radicals on a keratinous material, comprising applying a composition comprising, in a physiologically or pharmaceutically acceptable medium, at least one antioxidant having a structure comprising, in amino acid sequence from N-terminus to C-terminus:

tryptophan-X-tyrosine-X;

wherein

X is arginine, lysine, histidine or a positively-charged amino acid derivative, the C-terminal comprises carboxamide (—CONH2), each amino acid or amino acid derivative of the amino acid sequence is independently of a D- or L-configuration, and optionally, a peptide bond unit of the amino acid sequence is an isoster or surrogate peptide bond to a keratinous material in need of attenuation of effects of free radicals.

15. The method of claim 14, wherein X is arginine.

16. The method of claim 15, wherein each amino acid is in the L-configuration.

17. The method of claim 15, wherein at least one amino acid is in the D-configuration.

18. The method of claim 15, wherein the N-terminal amino group is acetylated.

19. The method of claim 14, wherein the antioxidant has the structure:

WRYR—NH2.

* * * * *